(12) United States Patent
Merk et al.

(10) Patent No.: US 6,348,630 B1
(45) Date of Patent: Feb. 19, 2002

(54) METHOD FOR PURIFYING HEXAMETHYLENEDIAMINE IN MIXTURES OF HEXAMETHYLENEDIAMINE AND AN UNSATURATED CYCLIC IMINE

(75) Inventors: Claudia Merk, Limburgerhof; Peter Bassler, Viernheim; Rolf Fischer, Heidelberg; Guido Voit, Freinsheim; Hermann Luyken, Ludwigshafen, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/720,915
(22) PCT Filed: Jul. 2, 1999
(86) PCT No.: PCT/EP99/04584
   § 371 Date: Jan. 2, 2001
   § 102(e) Date: Jan. 2, 2001
(87) PCT Pub. No.: WO00/02842
   PCT Pub. Date: Jan. 20, 2000

(30) Foreign Application Priority Data

Jul. 9, 1998 (DE) .......................................... 198 30 598

(51) Int. Cl.[7] ..................... C07D 223/04; C07D 295/02; C07D 227/02; C07C 211/02
(52) U.S. Cl. ..................... 564/498; 540/612; 540/484; 546/184; 546/185; 548/479; 204/157.71
(58) Field of Search ................... 540/484, 612, 540/184, 185; 548/579; 204/157.71; 564/498

(56) References Cited

U.S. PATENT DOCUMENTS 2,987,452 A    6/1961  Campbell .................... 202/57
4,282,381 A    8/1981  Buehler ...................... 564/498

FOREIGN PATENT DOCUMENTS

| CH | 393 353  | 10/1965 |
| EP | 497 333  | 8/1992  |
| WO | 93/02230 | 2/1993  |
| WO | 96/20166 | 7/1996  |

OTHER PUBLICATIONS

Ind.Org.Chem., 1988,S.266, Weissermel/Arpe.

Primary Examiner—Richard L. Raymond
Assistant Examiner—Kahsay Habte
(74) Attorney, Agent, or Firm—Keil & Weinakuf

(57) ABSTRACT

The level of an unsaturated cyclic imine (I) of the formula (I)

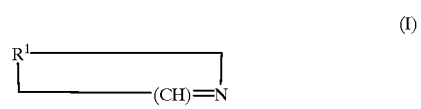

where $R^1$ is alkenyl having 3, 4, 5, 6, 7, 8, 9, 10, 11 carbon atoms belonging to the ring system, in a mixture comprising hexamethylenediamine and an imine (I) is reduced by electrochemical conversion of an imine (I) in a mixture comprising hexamethylenediamine and an imine (I) in the presence of solvated protons into a saturated cyclic amine of the formula (II)

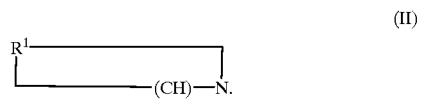

8 Claims, No Drawings

METHOD FOR PURIFYING HEXAMETHYLENEDIAMINE IN MIXTURES OF HEXAMETHYLENEDIAMINE AND AN UNSATURATED CYCLIC IMINE

DESCRIPTION

The present invention relates to a process for reducing the level of a unsaturated cyclic imine (I) of the formula (I)

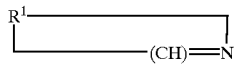

where $R^1$ is alkenyl having 3, 4, 5, 6, 7, 8, 9, 10, 11 carbon atoms belonging to the ring system, in a mixture comprising hexamethylenediamine and an imine (I) by electrochemical conversion of an imine (I) in a mixture comprising hexamethylenediamine and an imine (I) in the presence of solvated protons into a saturated cyclic amine of the formula II

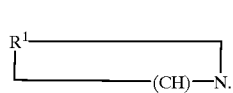

It is commonly known, for example from Weissermel/ Arpe, Industrielle Organische Chemie, Verlag Chemie, third edition, 1988, page 266, and WO-A-96/20166, to hydrogenate adiponitrile in the presence of ammonia under high pressure conditions over heterogeneous catalysts to form 6-aminocapronitrile (ACN) and/or hexamethylenediamine (HMD), which are both important intermediates for the manufacture of polyamides such as nylon-6 and nylon-6,6.

Depending on the catalyst used, this hydrogenation gives rise to varying amounts of undesirable by-products, such as tetrahydroazepine (THA), 1-amino-2-cyanocyclopentene (ICCP), 2-aminomethylcyclopentylamine (AMCPA), 1,2-diaminocyclohexane (DCH) and bishexamethylenetriamine (BHMTA), which—unlike the by-produced perhydroazepine (also known as hexamethyleneimine; HMI)—are very difficult to separate from the product of value, ACN and/or HMD.

For instance, U.S. Pat. No. 4,282,381 discloses (in column 2 of Table 1) that the hydrogenation of adiponitrile to form HMD in the presence of iron catalysts by-produces, inter alia, on average from 200 to 900 ppm of tetrahydroazepine.

High levels of THA necessitate a great deal of purification, by distillation, for example, which is reflected in considerable capital expenditure and energy costs or high chemical consumption, especially by complex hydrides such as $NaBH_4$ or $LiAlH_4$.

It is an object of the present invention to provide a process for reducing the THA content of mixtures comprising HMD and THA in a technically simple and economical manner.

We have found that this object is achieved by the process defined at the beginning. The unsaturated cyclic imine (I) is a compound of the formula

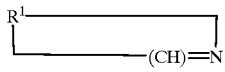

where
$R^1$ is an alkylene radical having 3, 4, 5, 6, 7, 8, 9, 10, 11 preferably 5, carbon atoms belonging to the ring system.

The alkylene radical may bear substituents; the alkylene radical is preferably a pure, preferably unbranched, hydrocarbon radical. Preferred alkylene radicals are the trimethylene, tetramethylene, pentamethylene, hexamethylene, heptamethylene, octamethylene, nonamethylene, decamethylene, undecamethylene groups, especially pentamethylene.

Compound (I) may be a mixture of different such imines, but preferably is one such imine.

The amines (II) obtainable by the process of the present invention generally have the same radical $R^1$ as the imines (II) used as starting material.

Compound (I) is particularly preferably THA of the formula

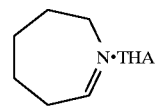

The process of the present invention converts it into perhydroazepine of the formula

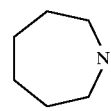

as compound (II).

According to the present invention, THA is used in mixtures comprising HMD and THA. Such mixtures are obtainable for example in the aforementioned hydrogenation of adiponitrile. The THA contents based on HMD range customarily from 100 to 2500, especially from 200 to 900, ppm.

A mixture comprising HMD and an imine (I) can be used for the conversion in pure form or preferably in mixtures with liquid diluents.

Advantageous liquid diluents are hydroxyl-containing compounds, preferably water or alcohols having from 1 to 4 carbon atoms, such as methanol, ethanol, 1-propanol, 2-propanol, 1-butanol, 2-butanol, 2-methylpropanol, 1-methylpropanol, preferably water or methanol, especially water, or mixtures thereof, and also mixtures of such hydroxyl-containing compounds with non-hydroxyl-containing compounds, preferably ethers, such as dimethoxyethane or tetrahydrofuran or mixtures thereof.

The amount of liquid diluent is easily ascertained in a few simple preliminary tests.

For an HMD/THA mixture having a THA content within the range from 100 to 2500, especially from 200 to 900, ppm, the presence of water and/or methanol, especially water, in an amount of from 0.01 to 20% by weight based on the total mixture will be particularly advantageous.

The electrochemical conversion is suitably carried out using electrolysis cells having one, preferably more than one, such as 2, 3 or 4, especially 2, cell compartments. If a plurality of cell compartments are used, the compartments are advantageously separated from each other by ion-permeable membranes.

In the case of 2 compartments, suitable membranes used are especially cation-permeable, especially proton-permeable, membranes.

Such membranes are commonly known and commercially available for example under the tradename Nafion, for example Nafion 324 (from DuPont).

The anode space advantageously has filled into it a liquid which, on application of a voltage to the electrolysis cell, is capable of forming solvated protons on the anode side. Suitable liquids include hydroxyl-containing compounds, such as water or acids, preferably organic acids, such as mono- or dicarboxylic acids, or their salts, and also their mixtures. To enhance the electrical conductivity, these liquids may be admixed with organic or inorganic bases, such as HMD, preferably inorganic acids, such as sulfuric acid, especially organic acids, such as adipic acid, in amounts from 0.1 to 2% by weight based on total liquid.

Such liquids typically form solvated protons, and evolve oxygen at the same time, on a voltage being applied to the electrolysis cell.

Anode materials for this elementary reaction of the electrolysis cell are known per se and commercially available. Materials which are advantageous to use include, for example, an Ru-Ta-Ti mixed oxide or an Ir-Ti mixed oxide, commercially available as Dendra DSA Elektrode or Heraeus Pita 64.

The cathode space of the electrolysis cell has filled into it a mixture comprising HMD and an imine (I).

To enhance the electrical conductivity, the cathode space may have introduced into it organic, preferably inorganic, salts, for example alkali metal halides such as lithium chloride, inorganic or organic bases or inorganic or organic acids, for example monocarboxylic acid, preferably dicarboxylic acids, especially adipic acid, in amounts from 0.1 to 2% by weight based on total catholyte.

Advantageously, the catholyte may include a material which is catalytically active for the reaction and which is preferably heterogeneous with regard to the catholyte, such as finely divided metal, preferably iron, Raney cobalt or Raney nickel, especially Raney nickel, in amounts from 1 to 20% by weight based on the catholyte. After the reaction, such catalytically active materials can be separated from the mixture in a conventional and simple manner, as by filtration.

Filter materials of the cathode for this elementary reaction of the electrolysis cell are known per se and commercially available. It may be advantageous to use metal filters such as stainless steel filters or filters composed of platinized titanium.

The reaction is customarily carried out at a temperature at which anolyte and catholyte are present in liquid form, preferably at from 10 to 60° C., especially at from 36 to 40° C.

The current density is advantageously from 1 to 30 MA/cm$^2$, preferably from 15 to 30 mA/cm$^2$, which results in voltages from 14.4 to 58 V, preferably from 14.4 to 36 V.

The compound (II) which is formed from the starting mixture of the invention, comprising HMD and imine (I), can be separated from the product mixture in a conventional manner, as by distillation, crystallization or extraction.

EXAMPLE

The examples were carried out under the following conditions:

TABLE 1

| Cell type | Divided cell, 2 compartments |
|---|---|
| Anode | Heraeus Pita 64, oxygen-evolving |
| Cathode | Edge gap element composed of platinized titanium, gap width: 100 μm |
| Electrode surface area | 100 cm$^2$ |
| Membrane | Nafion 324 |
| Electrolysis temperature | 38° C. |
| Anolyte | 1200 g of aqueous 1% strength sulfuric acid |
| Catholyte | Catalyst: 50 g of Raney nickel Remainder: see Table 2 |

TABLE 2

| | | | | | |
|---|---|---|---|---|---|
| HMD [g] | 1120 | 840 | 1120 | 1120 | 1120 |
| Methanol [g] | — | 560 | — | — | — |
| H$_2$O [g] | 280 | — | 280 | 280 | 180 |
| LiCl [g] | — | 28 | — | — | — |
| Adipic acid [g] | — | — | — | 21 | 21 |
| Current density [mA/cm$^2$] | 1.6–2.9 | 30 | 0.5–0.9 | 15 | 15 |
| Voltage (start) [V] | 58.0 | 14.4 | 57.9 | 36.8 | 47.6 |
| Voltage (end) [V] | 58.1 | 25.7 | 56.3 | 22.9 | 20.3 |
| THA start [ppm] | 1399 | 753 | 1530 | 775 | 829 |
| THA end [ppm] | 91/30 | 37 | 81/41 | 185/62/46 | 196/55/15 |
| Time [h] | 10/50 | 4 | 10/43 | 5/10/20 | 5/10/15 |
| THA reduced by [%] | 93/98 | 95 | 95/97 | 76/92/94 | 76/93/98 |

We claim:

1. A process for the purification of hexamethylenediamine from a mixture comprising hexamethylenediamine and an unsaturated cyclic imine (I) of the formula (I)

$$R^1-(CH)=N \quad (I)$$

where $R^1$ is alkenyl having 3, 4, 5, 6, 7, 8, 9, 10, 11 carbon atoms belonging to the ring system, the electrochemical conversion of the imine (I) in a mixture comprising hexamethylenediamine and the imine (I) in the presence of solvated protons into a saturated cyclic amine of the formula (II)

$$R^1-(CH_2)-N \quad (II)$$

and removing the saturated cyclic amine of formula (II).

2. The process of claim 1, wherein tetrahydroazepine is used as compound (I) to obtain perhydroazepine as compound (II).

3. The process of claim 1, wherein the conversion is carried out in the presence of water or of an alcohol having from 1 to 4 carbon atoms.

4. The process of claim 1, wherein the conversion is carried out in the presence of a catalyst.

5. The process of claim 4, wherein the catalyst used is Raney nickel.

6. The process of claim 1, wherein the conversion is carried out in the presence of an organic acid.

7. The process of claim 6, wherein the organic acid used is a mono- or dicarboxylic acid.

8. The process of claim 7, wherein the monocarboxylic acid used is adipic acid.

* * * * *

UNITED STATES PATENT AND TRADEMARK OFFICE
CERTIFICATE OF CORRECTION

PATENT NO.    : 6,348,630 B1
DATED         : February 19, 2002
INVENTOR(S)   : Merk et al.

It is certified that error appears in the above-identified patent and that said Letters Patent is hereby corrected as shown below:

<u>Title page,</u>
ABSTRACT, the formula II should read as follows:

Signed and Sealed this

Thirteenth Day of August, 2002

*Attest:*

*Attesting Officer*

JAMES E. ROGAN
*Director of the United States Patent and Trademark Office*